United States Patent [19]

Denzinger et al.

[11] 4,451,582

[45] May 29, 1984

[54] PREPARATION OF INSOLUBLE, ONLY SLIGHTLY SWELLABLE POLYMERS OF BASIC VINYL-HETEROCYCLIC COMPOUNDS

[75] Inventors: Walter Denzinger, Speyer; Hans-Helmut Goertz, Ludwigshafen; Axel Sanner, Frankenthal; Heinrich Hartmann, Limburgerhof, all of Fed. Rep. of Germany

[73] Assignee: BASF Aktiengesellschaft, Ludwigshafen, Fed. Rep. of Germany

[21] Appl. No.: 472,242

[22] Filed: Mar. 4, 1983

[30] Foreign Application Priority Data

Mar. 13, 1982 [DE] Fed. Rep. of Germany ....... 3209224

[51] Int. Cl.$^3$ .................. C08F 126/06; C08F 226/06; C08F 8/10; B01J 39/20
[52] U.S. Cl. ...................................... 521/38; 526/284; 526/285; 521/31; 560/1; 562/400; 562/483; 435/41; 435/188
[58] Field of Search ............... 526/284, 285, 258, 263, 526/264; 521/38

[56] References Cited

U.S. PATENT DOCUMENTS

| 2,878,183 | 0/0000 | Schuster et al. | |
| 3,689,439 | 0/0000 | Field et al. | |
| 3,754,055 | 8/1973 | Rembaum | 526/265 |
| 3,907,720 | 0/0000 | Field et al. | |
| 3,935,086 | 1/1976 | Misumi et al. | 521/38 |
| 3,935,086 | 0/0000 | Misumi et al. | |
| 3,992,562 | 11/1976 | Denzinger et al. | 526/211 |
| 3,992,562 | 0/0000 | Denzinger et al. | |
| 4,036,814 | 7/1977 | Howes et al. | 526/265 |
| 4,058,491 | 11/1977 | Steckler | 521/38 |

FOREIGN PATENT DOCUMENTS 2324204 of 0000 Fed. Rep. of Germany .

OTHER PUBLICATIONS

H. F. Kauffmann & J. W. Breitenbach, Angew. Makromol. Ch. 45, (1975), 167 to 175.
J. W. Breitenbach et al., Makromol. Ch. 177, (1976), 2787 to 2792.
W. Breitenbach, Encycl. of Polymer Science & Technology, vol. 11, 587 to 597.

Primary Examiner—Joseph L. Schofer
Assistant Examiner—Peter F. Kulkosky
Attorney, Agent, or Firm—Oblon, Fisher, Spivak, McClelland & Maier

[57] ABSTRACT

A process for the preparation of insoluble, only slightly swellable, granular polymers of basic vinyl-heterocyclic compounds and of their copolymers with up to 30% by weight of copolymerizable monomers and 0.1–10% by weight of crosslinking agent by exclusion of (atmospheric) oxygen from the mixture of monomer and crosslinking agent, without addition of any initiator or catalyst, and the use of the polymers obtained as ion exchangers, adsorbents and carriers for proteins.

18 Claims, No Drawings

PREPARATION OF INSOLUBLE, ONLY SLIGHTLY SWELLABLE POLYMERS OF BASIC VINYL-HETEROCYCLIC COMPOUNDS

It is known that homopolymers of N-vinylimidazoles and vinylpyridines, as well as copolymers of these monomers with N-vinyl-lactams, are readily soluble in water and in numerous organic solvents. It is also known that insoluble but swellable polymers of vinylimidazoles and vinylpyridines can be prepared by polymerizing the vinylheterocyclic compounds in a conventional manner in the presence of polyfunctional monomers (having two or more copolymerizable double bonds) which have a crosslinking action, and in the presence or absence of mono-unsaturated comonomers, free radical catalysts being added to the mixture as starters or initiators. Examples of suitable crosslinking agents are divinyl esters of dicarboxylic acids, eg. succinic acid and adipic acid, diacrylates of polyhydric alcohols, e.g. ethylene glycol and butanediol, and allyl ethers of polyhydric alcohols, e.g. pentaerythritol triallyl ether. Such crosslinking agents are not very simple to prepare and are therefore relatively expensive compared to mono-unsaturated monomers. Moreover, even if substantial amounts of the polyfunctional monomer are used, the swellability of the polymers in water is relatively high, so that on polymerization in aqueous solution a gel is formed.

For example, U.S. Pat. No. 2,878,183 teaches the preparation of very highly crosslinked and therefore insoluble, but nevertheless highly swellable, polyvinylimidazoles by free radical polymerization of N-vinylimidazoles in the presence of substantial amounts of polyfunctional monomers, the polymerization being carried out in water and the polymers being formed as gels. Such highly swellable gels have severe disadvantages in respect of their preparation, their general handling, and their use as ion exchangers or as carriers for reagents, such as enzymes or the like. During preparation they block the reaction vessel, they can neither be stirred nor poured out, and when they are being dried large quantities of solvent must be evaporated. For use, they must be preswollen and, in this condition, are not pourable; a column filled with the material tends to clog.

U.S. Pat. Nos. 3,689,439 and 3,907,720 describe the preparation of copolymers of N-vinyl-lactams with small amounts of N-vinylimidazoles by free radical polymerization in the presence of crosslinking agent, the polymerization being carried out in aqueous salt solutions of 10–20% strength. The polymers are obtained in the form of granules of diameter 1–7 mm. Disadvantages of this process are, inter alia, that the isolation of the polymers in a pure form from the salt solution is very expensive and that the polymer is obtained in a coarse, non-porous form and with a relatively low surface area.

German Pat. No. 2,324,204 describes a method for the preparation of poly-N-vinylimidazoles, wherein the polymerization is carried out in an organic solvent and it is very expensive to isolate the polymers in a solvent-free form.

U.S. Pat. No. 3,935,086 teaches that vinylimidazoles may be polymerized in the absence of solvents, by means of photoinitiation. Since the polymers are obtained in the form of films, their use is very restricted. Apart from shortcomings in their method of preparation, these polymers, because of their relatively high swellability, are only of limited usefulness as ion exchangers or protein carriers.

A process for the preparation of relatively slightly swellable polymers, even without addition of substantial amounts of crosslinking agents, is known in the literature by the name of, inter alia, popcorn polymerization (H. F. Kauffmann and J. W. Breitenbach, Angew. Makromol. Chem. 45 (1975), 167–175: N-vinylpyrrolidone and popcorn polymers; J. W. Breitenbach, H. F. Kauffmann and G. Zwilling, Makromol. Chem. 177 (1976), 2,787–2,792: acrylic acid popcorn polymers) or as proliferous polymerization (J. W. Breitenbach, Encycl. of Polymer Sci. and Technol. Vol. 11, 587–597). This type of polymerization, known in industry as a source of problems, as a rule leads to industrially unusable products with irregularly large particles. Hitherto, this process has not been disclosed for basic vinyl-heterocyclic compounds.

It is an object of the present invention to prepare, in a very simple manner and using very small amounts of (expensive) crosslinking agents having two or more copolymerizable double bonds, porous, granular, basis polymers which are only slightly swellable in water, are not gel-forming and are useful as ion exchangers and as adsorber resins (carriers), especially for proteins (particularly enzymes).

We have found that this object is achieved by use of the process as set out in the claims.

The polymers obtainable in accordance with the invention differ from normal polymers, i.e. from polymers obtained with the aid of conventional amounts of free radical initiators, or by photoinitiation, not only in that, for the same concentration of crosslinking agent, they swell substantially less in water, so that the amount of water absorbed by swelling is less than half, as a rule from one-third to one-seventh or even less, but also in the entire course of the polymerization, and especially in their optical (macroscopic and microscopic) appearance: a conventional polymerization without solvent gives a solid block, whilst in aqueous solution, if the monomer and polymer are water-soluble (as in the case in the present instance) a gel is obtained, whilst, using the process according to the invention, in both cases a porous, granular mass with a particle diameter of from about 10 to 500 $\mu$m is formed. If polymerization is carried out without stirring, the granules cake together to form a porous mass which can easily be broken up into crumbs. If, as is always preferred, stirring is employed during the polymerization, the granules agglomerate loosely to form irregularly shaped crumbs, whose average size depends on the intensity of stirring and is in most cases of the order of magnitude of from 0.1 to 5 mm diameter.

The polymerization of the monomer/crosslinking agent mixture commences as soon as the atmospheric oxygen has been completely removed, and does so spontaneously even at room temperature and even without having removed the polymerization inhibitors, for example hydroquinone, t-butylpyrocatechol or phenothiazine which are normally present in the monomers to increase their shelf life. Molecular oxygen appears to be the sole inhibitor which inhibits not only the normal free radical polymerization but also the polymerization according to the invention.

U.S. Pat. No. 3,992,562 discloses a process for the preparation of clarifiers for vegetable beverages, wherein mixtures of N-vinyl-lactams are polymerized with small amounts of a doubly unsaturated cyclic acid amide as a crosslinking agent, in the presence of certain sulfur compounds in dilute aqueous solution, using the same polymerization method as is employed according to the present invention. The polymers thus obtainable particularly efficiently adsorb tanning agents, but not proteins, and accordingly are unsuitable as carriers for enzymes and also for use as ion exchange resins.

It is the merit of the present invention that it has for the first time deliberately applied this type of polymerization, which was known per se for the case of other monomers but as a rule only viewed negatively because it was considered a nuisance, to basic vinylheterocyclic compounds and that it has thereby, surprisingly, achieved a technical advance. The invention provides a simple method of achieving the object stated above, i.e. to prepare basic polymers which are only slightly swellable in water and therefore not gel-forming (and which moreover also have the requisite large surface area), which are outstandingly useful as ion exchangers and adsorber resins and have a broad spectrum of use.

For the purposes of the invention, basic vinylheterocyclic compounds are saturated and aromatically unsaturated heterocyclic compounds having one vinyl group and one or more basic tertiary ring nitrogen atom with a pKa of greater than 4, preferably of from 5 to 8. In addition to the vinyl group, the ring may also carry alkyl groups of 1 to 4 carbon atoms, phenyl or benzyl groups or a fused second ring. Examples of suitable compounds are: N-vinylimidazole and its derivatives, e.g. 2-methyl-1-vinylimidazole, 4-methyl-1-vinylimidazole, 5-methyl-1-vinylimidazole, 2-ethyl-1-vinylimidazole, 2-propyl-1-vinylimidazole, 2-isopropyl-1-vinylimidazole, 2-phenyl-1-vinylimidazole and 1-vinyl-4,5-benzimidazole, of which N-vinylimidazole and 2-methyl-1-vinylimidazole are particularly preferred. Further examples of suitable compounds are 2-vinylpyridine, 4-vinylpyridine and 5-methyl-2-vinylpyridine. Of course, mixtures of basic vinyl-heterocyclic compounds may also be employed.

The crosslinking agent is used in an amount of from 0.1 to 10%, preferably from 1 to 4%, based on the total monomer weight. Suitable crosslinking agents are those which contain two or more copolymerizable groups in the molecule. Particularly suitable compounds are alkylene-bis-acrylamides, e.g. methylene-bis-acrylamide and N,N'-bis-acryloyl-ethylenediamine, as well as N,N'-divinylethyleneurea, N,N'-divinylpropyleneurea, ethylidene-bis-3-(N-vinylpyrrolidone), N,N'-divinyl-(2,2')-diimidazolyl and 1,1'-bis-(3,3'-vinylbenzimidazolid-2-one)-1,4-butane. Examples of other useful crosslinking agents are alkylene glycol diacrylates and dimethacrylates, e.g. ethylene glycol diacrylate and dimethacrylate and tetramethylene glycol diacrylate and dimethacrylate, aromatic divinyl compounds, e.g. divinylbenzene and divinyltoluene, allyl acrylate, divinyldioxane, pentaerythrityl triallyl ether and mixtures of these. If the polymerization is carried out in water, of course only those crosslinking agents which are soluble in the aqueous monomer mixture are suitable.

The same remark of course also applies to the comonomers which may be used in amounts of up to 30, preferably up to 20, % by weight, based on the total monomer mixture. Examples of suitable comonomers are styrene, acrylic esters, vinyl esters, acrylamide and, preferably, N-vinyl-lactams, e.g. 3-methyl-N-vinylpyrrolidone, N-vinylcaprolactam and especially N-vinylpyrrolidone.

To carry out the polymerization without a solvent, the monomer mixture consisting of the basic vinyl-heterocyclic compound and the crosslinking agent, with or without N-vinyl-lactam or some other comonomer, is rendered inert by passing nitrogen through it and is then heated at 100°-200° C., preferably 150°-180° C. It is advantageous to continue to pass a slight stream of nitrogen into the mixture. It is particularly advantageous to cause the batch to boil by applying reduced pressure. Depending on the nature of the monomers employed and on the temperature chosen, the mixture will then polymerize within 1-20 hours. For example, on polymerizing 2-methyl-1-vinylimidazole with 2% of N,N'-divinylethyleneurea at 150° C. and a pressure of 310 mbar, while stirring with a powerful stirrer, the first polymer particles form after 2.5 h and slowly grow until, after 10 h, the batch consists of a brownish powder. After having been washed with water and dried, the new polymer is obtained, in yields of more than 90%, in the form of a coarse powder.

A preferred method of preparation is precipitation polymerization in water. The concentration of the monomers in the reaction batch is advantageously so chosen that the batch remains easily stirrable over the entire duration of the reaction. If insufficient water is added, the polymer granules become tacky so that stirring becomes more difficult than if water is entirely absent. Using the conventional stirred kettles, the appropriate monomer concentration, based on the aqueous mixture, is about 5-30, preferably 10-20, % by weight. It can be increased to as much as 50% by weight if powerful stirrers are available. It can also be advantageous to start the polymerization with a relatively concentrated solution and then to dilute it with water as the reaction proceeds. The polymerization may, where appropriate, advantageously be carried out at a pH above 6 in order to avoid possible hydrolysis of the comonomers and/or crosslinking agents. The pH may be adjusted by adding small amounts of bases such as sodium hyroxide or ammonia or the conventional buffer salts such as sodium carbonate, sodium bicarbonate or sodium phosphate. Exclusion of oxygen may be achieved by keeping the polymerization batch at the boil and/or, as already mentioned, by using an inert gas such as nitrogen. The polymerization temperature may be from 20° to 150° C., preferably from 50° to 100° C.

In some cases it can be advantageous, in order completely to remove dissolved oxygen, to add small amounts—from 0.1 to 1% by weight, based on the monomer mixture—of a reducing agent such as sodium sulfite, sodium pyrosulfite, sodium dithionite, ascorbic acid or the like.

In a particularly preferred embodiment of precipitation polymerization, the water-soluble comonomer (preferably an N-vinyl-lactam), a part of the crosslinking agent, water and, where appropriate, a buffer and a reducing agent, are heated in a slight stream of nitrogen until the first polymer particles are visible. A mixture, which has beforehand been rendered inert by passage of nitrogen, of the vinyl-heterocyclic compound and the remainder of the crosslinking agent, with or without water as the diluent, is then added over 0.2-2 hours. This method has the advantage that it shortens the polymerization time.

The polymer, which is obtained in about 90-95% of the theoretical yield, may be isolated from the aqueous suspension by filtering or centrifuging, followed by washing with water and drying in conventional driers such as through-circulation drying ovens, vacuum drying ovens, paddle driers or flow driers.

Because of their basic nitrogen content, the novel polymers may be used in the non-quaternized form as weak anion exchangers and in the quaternized form as strong anion exchangers. Converting them to the quaternized form with conventional quaternizing reagents such as methyl iodide or benzyl chloride leads to exchange capacities of up to about 6 milliequivalents/g (chloride form). Apart from their usefulness as ion exchangers, the polymers claimed can be generally employed as adsorber resins. For example, they adsorb phenolic substances such as tannin. They may also be used to remove colored concomitant materials from sugar solutions by adsorption. Moreover, the polymers very effectively adsorb proteins, especially enzymes, which in many cases retain a substantial proportion of their activity even after adsorption. They may therefore be employed, with the enzyme adsorbed thereon, as a heterogeneous catalyst for the reaction of the particular enzyme. Particularly preferred enzymes for such application are invertase, glucose-isomerase, amyloglucosidase, alpha- and beta-amylase, aminoacid-acylase, penicillin-acylase and hydantoinase. Other suitable enzymes are oxido-reductases, e.g. alcohol-dehydrogenase, lactate-dehydrogenase, aminoacid-oxidase, peroxidase, catechol-oxidase, monoamino-oxidase, lipoxygenase, luciferase, nitrate-reductase, nitrite-reductase, chloroperoxidase, acetaldehyde-dehydrogenase, aldehyde-oxigenase, diaphorase, cholesterol-oxidase, glutarothioreductase, hydroxysteroid-dehydrogenase, xanthin-oxidase, dopamine-hydroxylase, cytochrome-oxidase, monoamino-oxidase, diacetyl-reductase, peroxide-dismutase and limonate-dehydrogenase; transferases, e.g. polynucleotide-phosphorylase, dextran-sucrase, phosphorylase, carbamate-kinase, amino-transferase, transaldolase, methyl-transferase, pyruvate-kinase, carbomyl-transferase, phosphofructokinase and dextran-synthetase; hydrolases, e.g. lipase, esterase, lactase, lysozyme, cellulase, urease, trypsin, chymotrypsin, glutaminase, asparaginase, papaine, ficin, pepsin, leucine-aminopeptidase, carboxypeptidases A+B, naringinase, bromelaine, subtilisin, phospholipase, isoamylase, cephalosporin-amidase, adenosine-deaminase, penicillinase, maltase, dextranase, desoxy-ribonuclease, sulfatase, pullulanase, phosphatase, alpha-galactosidase, dextranase and beta-glucanase; lyases, e.g. tryptophanase, tryosine-decarboxylase, oxynitrilase, phenylalanine-decarboxylase, pyruvate-decarboxylase, fumarase, enolase, aspartase, aminolevuline-dehydratase and carboanhydratase; isomerases, e.g. amino-acid-racemase and triosephosphate-isomerase; and ligases, e.g. glutahione-synthetase.

Because of the tendency of the cyclically bonded basic nitrogen to form complexes with transition metals, the polymers obtainable according to the invention are capable of bonding transition metal ions, for example Cu, Zn, Fe, Co, Ni, Ru, Rh, Pd and Pt, in various oxidation levels. These complexes can be used as catalysts in various reactions. For example, German Laid-Open Application DOS No. 2,437,133 describes the carboxylation of alcohols in the presence of polyvinylpyridine-copper complexes. The use of pyridine-palladium complexes as catalysts in the preparation of isocyanates is known, for example, from German Published Application DAS No. 2,416,683. Moreover, U.S. Pat. No. 3,652,676 mentions a polyvinylpyridine-transition metal complex as a hydroformylation catalyst.

Further fields of use of insoluble polymers containing basic nitrogen are disclosed in the literature. For example, it is known that polymers which contain imidazole rings greatly accelerate the hydrolysis of, for example, carboxylic acid esters (R. L. Letsinger et al., J. Amer. Chem. Soc. 84 (1962) 3,122). Polymers containing pyridine rings are very useful for accelerating acylation reactions, and at the same time serve to bond acid. Moreover, adducts of polyvinylpyridine with bromine can be used for brominations, whilst adducts with chromic acid can be used for oxidations (J. M. Frechet et al., J. Macromol. Sci. Chem. 11 (1977), 507; J. M. Frechet et al., J. Org. Chem. 43 (1978), 2,618).

In the Examples, parts and percentages are by weight.

EXAMPLE 1

100 parts of freshly distilled 2-methyl-1-vinylimidazole and 2 parts of N,N'-divinylethyleneurea were boiled at 150° C. under a pressure of 310 mbar in a stirred vessel with reflux condenser. After 2.5 hours, small polymer particles were discernible in the originally clear liquid and these slowly grew. After the batch had been stirred for 10 hours, it consisted of a dry powder. This was taken up in 1,000 parts of water, filtered off under suction, washed with 500 parts of water and dried in a through-circulation drying oven at 50° C., to give 92 parts of a slightly brownish polymer.

EXAMPLE 2

Using the method of Example 1, 75 parts of N-vinylimidazole, 25 parts of N-vinylpyrrolidone and 3 parts of N,N'-divinylethyleneurea were boiled at 180° C. and 250 mbar, with stirring. After about 1 hour, the first polymer particles were discernible, and these grew rapidly. After the batch had been stirred for 2 hours, it consisted of a dry powder. Washing and drying gave 94 parts of a pale yellow polymer.

EXAMPLE 3

150 parts of freshly distilled N-vinylimidazole, 3 parts of N,N'-divinylethyleneurea and 50 parts of water were boiled at about 100° C. in a stirred vessel with reflux condenser. After about 3 hours, the first polymer particles formed and after 3.5 hours the batch consisted of a thick polymer slurry. It was then diluted with 500 parts of water, after which the polymer particles continued to grow. The reaction was complete after a total of about 7 hours. The polymer was then filtered off with suction, washed with water and dried in an oven under reduced pressure at 50° C. The polymer was in the form of almost white, irregularly shaped agglomerate particles of 0.5–2 mm diameter. The yield was 92%.

EXAMPLE 4

60 parts of N-vinylpyrrolidone, 1.2 parts of N,N'-divinylethyleneurea, 540 parts of distilled water and 6.65 ml of 0.1 N sodium hydroxide solution were boiled in a stirred apparatus. After 15 minutes, insoluble polymer particles precipitated from the solution. A mixture of 540 parts of freshly distilled N-vinylimidazole and 10.8 parts of N,N'-divinylethyleneurea was then added over 1.5 hours, causing very rapid growth of the polymer particles. To keep the suspension stirrable, it was diluted with 200 parts of distilled water after 1 hour and again after 2 hours and 3 hours. After a total of 5 hours at 100° C., the polymerization was complete. The copolymer was in the form of a moist powder. It was taken up in 2,000 parts of water, centrifuged off, washed with 2,000 parts of water and dried in an oven under reduced pressure at 50° C. The polymer was in the form of almost white, irregularly shaped aggregates of 0.1–3 mm diameter. The yield was 90%.

15 parts of the polymer obtained according to Example 4 and 25 parts of methyl iodide in 200 parts of ethanol were heated for 5 hours at 60° C. The product was then filtered off under suction, washed with ethanol and dried under reduced pressure at 50° C. After conversion to the chloride form, the quaternized polymer had an anion exchange capacity of 5.0 milliequivalents/g.

EXAMPLE 5

60 parts of 4-vinylpyridine, 1.2 parts of N,N'-divinylethyleneurea, 540 parts of distilled water and 6.8 parts of 0.1 N sodium hydroxide solution were heated at 80° C. in a stirred apparatus. Throughout the reaction time, a slight stream of nitrogen was passed over the mixture. After 8 hours, the polymer was in the form of a thick suspension. It was filtered off under suction and washed with 2,000 parts of water. Drying at 50° C. in an oven under reduced pressure gave an almost white, granular product in a yield of 90%.

EXAMPLE 6

The polymerization was carried out as in Example 4, except that 2-methyl-1-vinylimidazole was used as the monomer and N,N'-divinylpropyleneurea as the crosslinking agent. The yield was 96%. Quaternizing a portion of the polymer by the method of Example 4 gave an anion exchange capacity of 5.1 milliequivalents/g.

100 mg of the non-quaternized polymer were stirred in 100 ml of an 0.01% strength tannin solution. After 10 minutes, the tannin concentration was determined photometrically in the supernatant liquor. At this point in time, 20% of the tannin had already been adsorbed on the polymer; after 40 minutes the figure was 70%.

7 g of the non-quaternized polymer were stirred for 2 days in 70 ml of a 1% strength solution of invertase. After this time, 90% of the enzyme had been bonded. The polymer was then transferred into a column and a 64% strength sucrose solution was passed over it at 30° C., at a flow rate of 100 ml/h. The degree of hydrolysis of the sucrose was 81% after 20 days, 80% after 40 days and 80.5% after 60 days.

EXAMPLE 7

15 parts of vinylpyrrolidone, 0.45 part of divinylethyleneurea, 135 parts of water and 1.65 parts of 0.1 N sodium hydroxide solution were heated at 85° C. under a stream of nitrogen in a stirred apparatus. 0.03 part of sodium dithionite, dissolved in 10 parts of water, was then added and after about 40 minutes, when insoluble polymer particles were distinctly discernible, a mixture of 120 parts of 1-vinyl-2-methylimidazole, 15 parts of methyl acrylate, 4.05 parts of methylene-bis-acrylamide and 500 parts of water was added over 20 minutes. Heating was then continued for 1 hour at 85° C. After the thick polymer slurry had cooled, the polymer was filtered off, washed with water and dried at 50° C. in an oven under reduced pressure. The polymer was in the form of white, irregularly shaped aggregates of about 0.1–5 mm diameter. The yield was 93.5%.

EXAMPLE 8

The polymerization was carried out as in Example 7, but after polymer particles had formed in the initial charge a mixture of 1.05 parts of 1-vinyl-2-methylimidazole, 30 parts of vinyl acetate, 4.05 parts of N,N'-bis-acryloylethylenediamine and 500 parts of water was added. The yield was 82.5%.

COMPARATIVE EXAMPLE

Crosslinked Polyvinylimidazole Prepared Using A Free Radical Catalyst 100 parts of vinylimidazole, 2 parts of N,N'-methylene-bis-acrylamide and 2 parts of azo-diisobutyronitrile were dissolved in 500 parts of water and the mixture was heated at 80° C. for 4 hours. The resulting stiff gel was dried under reduced pressure at 50° C. A glassy polymer was obtained in virtually quantitative yield. To determine the swelling characteristics, the polymer was comminuted and a sieve fraction of 250–500 μm was swollen in water for 2 hours. The swollen polymer was thoroughly drained on a suction filter, weighed moist, dried at 80° C. under reduced pressure and again weighed. A water absorption of 12.9 g/g of polymer was found.

Tested in the same way, a polymer prepared according to Example 4 had a water absorption of 1.7 g/g of polymer.

We claim:

1. A process for the preparation of insoluble, only slightly water-swellable, granular polymers of a basic vinyl-heterocyclic compound having a pKa of greater than 4, and of their copolymers with up to 30% by weight of copolymerizable monomers selected from the group consisting of styrene, acrylic esters, vinyl esters, acrylomide and N-vinyl-lactams, by polymerizing the monomers, wherein the following measures are employed simultaneously:

(a) 0.1–10% by weight, based on the total amount of monomer, of a crosslinking agent which crosslinks through its double bonds is employed, (b) oxygen organic solvent is excluded and (c) polymerization by irradiation or initiators are excluded.

2. A process as claimed in claim 1, wherein the polymerization is carried out in the presence of water at from 20° to 150° C.

3. A process as claimed in claim 1, wherein the polymerization is carried out without a solvent at from 100° to 200° C.

4. A process as calimed in claim 1, wherein the polymerization is carried out in the presence of a reducing agent.

5. A process as claimed in claim 1, wherein the basic vinyl-heterocyclic compound employed is 1-vinylimidazole or 2-methyl-1-vinylimidazole.

6. A process as claimed in claim 1, wherein the basic vinyl-heterocyclic compound employed is 2-vinylpyridine, 4-vinylpyridine or 2-methyl-5-vinylpyridine.

7. A process as claimed in claim 1, wherein the comonomer employed is an N-vinyl-lactam.

8. A process as claimed in claim 1, wherein the comonomer employed is N-vinylpyrrolidone.

9. A process as claimed in claim 1, wherein the crosslinking agent employed is N,N'-divinylethyleneurea.

10. A process as claimed in claim 1, wherein, after the polymerization, the basic nitrogen atoms of the vinyl-heterocyclic compounds are completely or partially quaternized with a conventional alkylating agent.

11. A process for ion exchange, wherein a polymer prepared as claimed in claim 1 is used as the ion exchanger.

12. A process for adsorbing chemical substances from their solutions, wherein a polymer prepared as claimed in claim 1 is used as the adsorbent.

13. A process for adsorbing proteins from aqueous solutions, wherein a polymer prepared as claimed in claim 1 is used as the adsorbent.

14. A process for immobilizing enzymes, wherein a polymer prepared as claimed in claim 1 is used as the adsorbent.

15. A process for carrying out an enzymatic reaction in an aqueous medium, wherein an enzyme-immobilizate prepared as claimed in claim 14 is used as the heterogeneous catalyst.

16. A process for adsorbing transition metals from aqueous solutions of their salts, wherein a polymer prepared as claimed in claim 1 is used as the adsorbent.

17. A process for hydrolyzing carboxylic acid esters, wherein a polymer prepared as claimed in claim 1 is used as the catalyst.

18. An acylation process, wherein a polymer prepared as claimed in claim 1 is used as the catalyst and acid-bonding agent.

* * * * *